(12) United States Patent
Yoon et al.

(10) Patent No.: US 12,313,542 B2
(45) Date of Patent: May 27, 2025

(54) GADGET FOR MEASURING RETROREFLECTED SIGNAL

(71) Applicant: AJOU UNIVERSITY INDUSTRY-ACADEMIC COOPERATION FOUNDATION, Suwon-si (KR)

(72) Inventors: Hyun Chul Yoon, Seoul (KR); Ka Ram Kim, Suwon-si (KR); Kyung Won Lee, Hwaseong-si (KR); Jae-Ho Kim, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 110 days.

(21) Appl. No.: 18/276,320

(22) PCT Filed: Feb. 10, 2022

(86) PCT No.: PCT/KR2022/002038
§ 371 (c)(1),
(2) Date: Aug. 8, 2023

(87) PCT Pub. No.: WO2022/182023
PCT Pub. Date: Sep. 1, 2022

(65) Prior Publication Data
US 2024/0125698 A1    Apr. 18, 2024

(30) Foreign Application Priority Data
Feb. 23, 2021  (KR) .......... 10-2021-0023794

(51) Int. Cl.
*G01N 21/55* (2014.01)
*G01N 33/487* (2006.01)
*G01N 21/17* (2006.01)

(52) U.S. Cl.
CPC .......... *G01N 21/55* (2013.01); *G01N 33/487* (2013.01); *G01N 2021/177* (2013.01); *G01N 2021/551* (2013.01)

(58) Field of Classification Search
CPC ...... G01N 21/55; G01N 21/47; G01N 33/487; G01N 33/4833; G01N 2021/177; G01N 2021/551; G01N 27/26; G01N 15/1434
(Continued)

(56) References Cited

U.S. PATENT DOCUMENTS

| | | | | |
|---|---|---|---|---|
| 5,316,727 A | * | 5/1994 | Suzuki | G01N 21/272 356/41 |
| 2003/0119202 A1 | * | 6/2003 | Kaylor | G01N 33/54388 436/514 |

(Continued)

FOREIGN PATENT DOCUMENTS

| KR | 10-2155218 B1 | 9/2020 |
|---|---|---|
| KR | 10-2179088 B1 | 11/2020 |

*Primary Examiner* — Hoa Q Pham
(74) *Attorney, Agent, or Firm* — Sughrue Mion, PLLC

(57) ABSTRACT

A gadget for retroreflected signal measurement is disclosed. The gadget for measuring the retroreflected signal includes a partitioning wall; a portable terminal receiving portion disposed on one surface of the partitioning wall; a biosensor receiving portion disposed on the other surface of the partitioning wall and constructed to receive a biosensor therein; a light exit channel defined in the partitioning wall and at one side thereof; and a light-receiving channel adjacent to the light exit channel and defined in the partitioning wall, wherein light passes through the light exit channel and then is reflected from the biosensor, and then is incident into the light-receiving channel.

10 Claims, 7 Drawing Sheets

(58) Field of Classification Search
USPC .............................. 356/244, 246, 432–440
See application file for complete search history.

(56) References Cited

U.S. PATENT DOCUMENTS

2005/0145491 A1* 7/2005 Amano ............ G01N 33/48757
204/403.02
2006/0216832 A1* 9/2006 Nishikawa ......... G01N 21/8483
436/514

* cited by examiner

GADGET FOR MEASURING RETROREFLECTED SIGNAL

CROSS REFERENCE TO RELATED APPLICATIONS

This application is a National Stage of International Application No. PCT/KR2022/002038 filed Feb. 10, 2022, claiming priority based on Korean Patent Application No. 10-2021-0023794 filed Feb. 23, 2021.

FIELD

The present disclosure relates to a gadget for retroreflected signal measurement. More particularly, the present disclosure relates to a gadget for retroreflected signal measurement that may be used as point-of-care analysis equipment.

DESCRIPTION OF RELATED ART

Methods that have been used with high frequency in industry and academia to perform quantitative/qualitative analysis of biological analysis targets, including immunological and molecular diagnosis have been performed in an optical system suitable for the principle of signal strength detection of a signal probe that causes color development, chemiluminescence, and fluorescence. This type of optical biosensing method meets high sensitivity of analysis and has various usability, but requires expensive analysis equipment equipped with sophisticated optical equipment in terms of experimental environment.

Moreover, a series of equipment for performing this analysis method has been miniaturized and simplified as needed, and diversified from automated blood analyzers used in central analysis rooms in large hospitals to a benchtop sized device that may be operated in medical staffs offices. However, the point-of-care diagnostic equipment which is used to quickly derive diagnostic results of the infectious diseases is generally based on fluorescence analysis equipment for diversification of target substances and high-sensitivity analysis for immunological and molecular diagnosis as required in a current diagnostic test market. However, the fluorescence analysis equipment has following problems.

1) Limitations of Conventional Optical System Including Light Source for Fluorescent Signal Induction and Detection Fluorescent dyes which are widely used as optical probes for immunoassays, provide effective signals only in response to excitation light of a specific wavelength. Thus, the fluorescence analysis equipment uses, as a light source, a combination of a halogen lamp that provides an entire wavelength range and a monochromator (or an excitation filter) that irradiates a specific wavelength selected from the entire range, or a high-power laser and LED that provides a short wavelength. In this way, a well-aligned light source may be provided. However, this light source is expensive and require high power consumption. Thus, compactness, portability, and commercialization of the optical system including the same are limited.

2) Limitations of Conventional Light Receiver and Optical Analysis System for Optical Signal Induction and Detection of Optical Probe A signal emission process as a conventional signal analysis principle in which a phosphor as an optical probe is excited by light from the light source and emits light of a wavelength may be stable by itself, but has a limitation that a filter system that selects the excitation light and a wavelength of the emitted light should necessarily exist in the optical system. The filter has a function of transmitting therethrough, reflecting, or blocking only a specific wavelength, and thus selectively transmits therethrough only a signal generated in the light emitting process such that the signal reaches the light receiver. The filter is essentially included in an optical path from the light source to the phosphor of the analysis target sample to the filter to the light receiver.

Moreover, for sensitive detection of the fluorescence signal, it is essential to employ expensive light-receiving equipment such as a photomultiplier tube (PMT). In addition, very sophisticated arrangement and assembly between the optical parts are required. This acts as a limiting factor in the miniaturization of an optical biosensor and realization of a device for on-site diagnosis.

3) Structural Limitations of Conventional Signal Detector Using Optical Probe

The conventional optical system for performing signal detection of the biosensor acts as a limiting factor in development of compact point-of-care equipment not only due to the complexity of components for the light receiver and the optical analysis system but also in that the conventional optical system may additionally require an external power source to drive the components. A short-wavelength light source and a high-sensitivity light-receiving element may be attached to a smart handset. This may secure stable performance thereof. However, research results indicating that in order to cope with the power consumption consumed in the analysis process, an external power supply should stably provide a large amount of power rather than using a lithium-ion battery of the smart handset itself were presented to the academic world. However, this is undesirable in that the smart handset is doubled due to the weight of the attachments to the smart handset.

DISCLOSURE

Technical Purpose

Therefore, a purpose of the present disclosure is to provide a gadget for retroreflected signal measurement which may be simply connected to a portable terminal carried by an individual and may be capable of quantitative analysis of a target bio-substance via a biosensor using retroreflective Janus particles (RJP) causing retroreflection as a signal probe, and thus may be used as an on-site diagnosis type analysis equipment.

Technical Solution

One aspect of the present disclosure provides a gadget for measuring a retroreflected signal, the gadget comprising: a partitioning wall; a portable terminal receiving portion disposed on one surface of the partitioning wall; a biosensor receiving portion disposed on the other surface of the partitioning wall and constructed to receive a biosensor therein; a light exit channel defined in the partitioning wall and at one side thereof; and a light-receiving channel adjacent to the light exit channel and defined in the partitioning wall, wherein light passes through the light exit channel and then is reflected from the biosensor, and then is incident into the light-receiving channel.

In one embodiment, the biosensor may include retroreflective Janus particles, and a sensing substrate, wherein each of the retroreflective Janus particles may include: a transparent core particle; a total-reflective coating layer covering a portion of the core particle; and a first biorecognition substance directly or indirectly binding to an exposed surface of the core particle, wherein the sensing substrate may include: a transparent bottom whose a surface is modified with a second biorecognition substance selectively reacting with a target bio-substance; a cover opposite to the bottom and having an injection hole defined therein through which a detection target solution is injected into the sensing substrate; a sidewall disposed between the cover and the bottom, and having a through opening defined therein; and a fluid channel defined by the bottom, the cover and the sidewall, wherein each of the retroreflective Janus particles may be oriented so that the exposed surface of the core particle thereof faces the bottom of the sensing substrate, wherein the biosensor may be accommodated in the biosensor receiving portion so that the bottom faces the light exit channel and the light-receiving channel.

In one embodiment, the portable terminal receiving portion may accommodate therein an upper end of the portable terminal where a camera and a flash of the portable terminal are disposed, wherein the light exit channel may be disposed so as to face the flash, wherein the light-receiving channel may be disposed so as to face the camera.

In one embodiment, the light exit channel may act as a first opening through which light from the flash passes through the partitioning wall, wherein the light-receiving channel may act as a second opening through which light passes through the partitioning wall and is incident to the camera.

In one embodiment, the gadget may further comprise a magnifying lens disposed between the second opening and the biosensor.

In one embodiment, the biosensor receiving portion may include: a sensor receiving cover protruding outwardly from the other surface of the partitioning wall, wherein an inner space is defined by the cover and accommodates the biosensor therein; and a biosensor support disposed in the inner space defined by the sensor receiving cover and disposed so as to face the light-receiving channel, wherein the biosensor is mounted into the biosensor support.

In one embodiment, the sensor receiving cover may have a sensor receiving opening defined in a side portion thereof, wherein the biosensor support may have a rail structure extending from the sensor receiving opening to the inner space defined by the sensor receiving cover, wherein the biosensor may be slidably inserted into the rail structure.

In one embodiment, the gadget may further comprise a light outlet channel disposed behind the biosensor receiving portion and disposed so as to face the biosensor receiving portion.

In one embodiment, the gadget may further comprise a light outlet channel defined in a rear portion of the sensor receiving cover and disposed so as to face the biosensor receiving portion.

In one embodiment, the light outlet channel may act as a third opening disposed in the rear portion of the sensor receiving cover.

In one embodiment, the third opening may have a length greater than or equal to a length of the biosensor support.

Technical Effect

According to the gadget for retroreflected signal measurement according to the present disclosure, the portable optical measurement equipment using retroreflection as a biosensing principle may be implemented so as not to employ fluorescence analysis used as a conventional optical analysis principle. Further, the gadget for retroreflected signal measurement may be simply connected to the portable terminal carried by an individual and may be capable of quantitative analysis of the target bio-substance via the biosensor using the retroreflective Janus particles (RJP) causing retroreflection as a signal probe, and thus may be used as an on-site diagnosis type analysis equipment.

DETAILED DESCRIPTIONS

Figure 1:
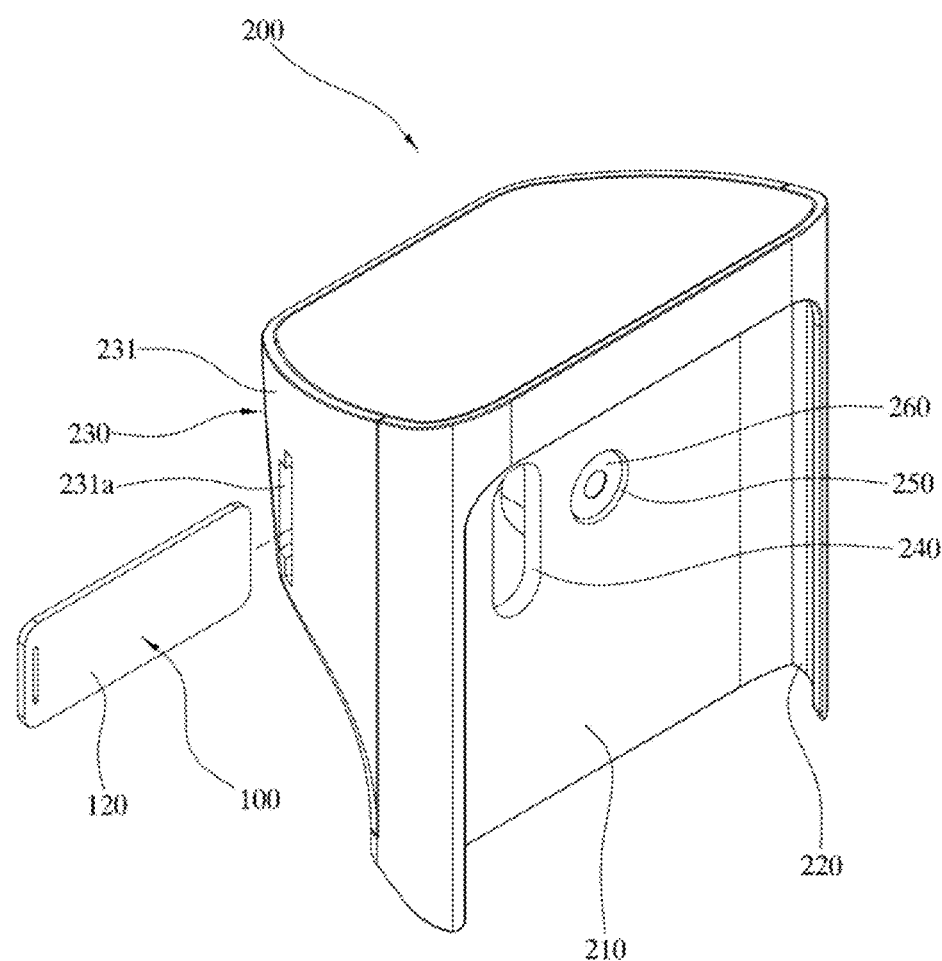
FIG. 1 is a perspective view showing a configuration of a gadget for measuring a retroreflected signal according to an embodiment of the present disclosure.

Hereinafter, a gadget for measuring a retroreflected signal according to an embodiment of the present disclosure will be described in detail with reference to the accompanying drawings. The present disclosure may have various changes and may have various forms. Thus, specific embodiments are illustrated in the drawings and described in detail in the text. However, this is not intended to limit the present disclosure to the specific forms as disclosed. It should be appreciated that the present disclosure includes all modifications, equivalents, or substitutes included in the spirit and scope of the present disclosure. Like reference numerals have been used for like elements throughout the descriptions of the drawings. For simplicity and clarity of illustration, elements in the drawings are not necessarily drawn to scale.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described under could be termed a second element, component, region, layer or section, without departing from the spirit and scope of the present disclosure.

The terminology used herein is directed to the purpose of describing particular embodiments only and is not intended to be limiting of the present disclosure. As used herein, the singular constitutes "a" and "an" are intended to include the plural constitutes as well, unless the context clearly indicates otherwise. It will be further understood that the terms "comprise", "comprising", "include", and "including" when used in this specification, specify the presence of the stated features, integers, operations, elements, and/or components, but do not preclude the presence or addition of one or more other features, integers, operations, elements, components, and/or portions thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
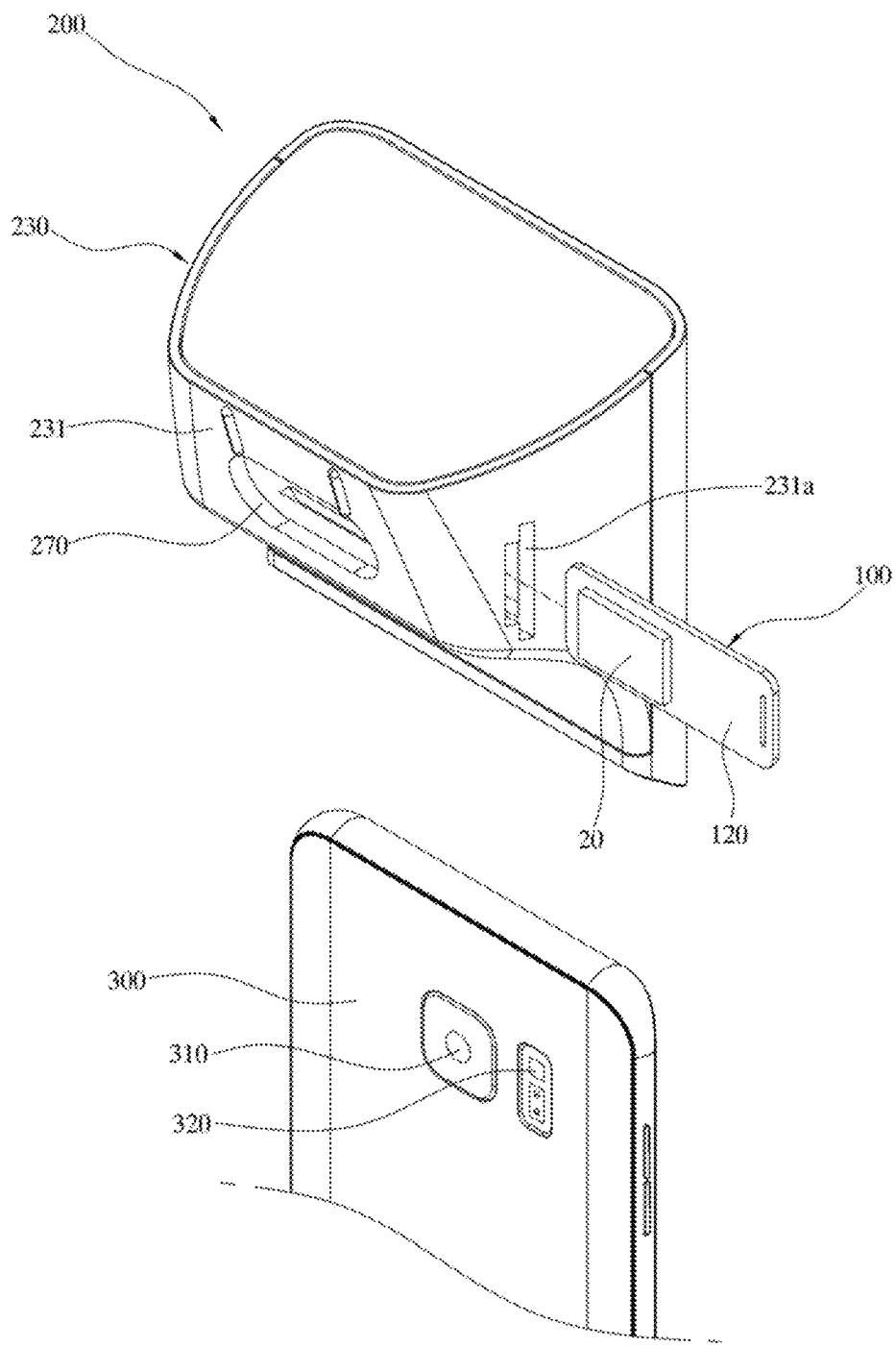
FIG. 2 is a rear perspective view of FIG. 1.
Figure 3:
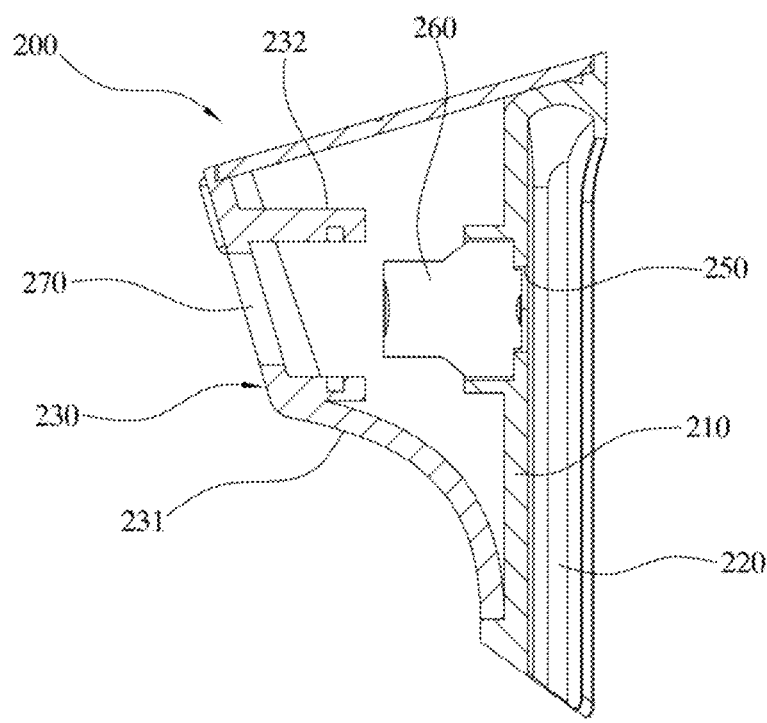
FIG. 3 is a cross-sectional view of FIG. 1.

FIG. 1 is a perspective view showing the configuration of a gadget for measuring a retroreflected signal according to an embodiment of the present disclosure. FIG. 2 is a rear perspective view of FIG. 1. FIG. 3 is a cross-sectional view of FIG. 1.

Referring to FIG. 1 to FIG. 3, a gadget 200 for measuring a retroreflected signal according to an embodiment of the present disclosure includes a partitioning wall 210; a portable terminal receiving portion 220 disposed on one surface of the partitioning wall 210; a biosensor receiving portion 230 disposed on the other surface of the partitioning wall 210 and constructed to accommodate a biosensor 100 therein; a light exit channel 240 defined in one side of the partitioning wall 210; and a light-receiving channel 250 adjacent to the light exit channel 240 and defined in the partitioning wall 210, wherein light passes through the light exit channel 240 and then is reflected from the biosensor 100 and then is incident into the light-receiving channel 250.

The partitioning wall 210 is disposed between the portable terminal receiving portion 220 and the biosensor receiving portion 230 and divides a space of the gadget into a space where the portable terminal is disposed and a space where the biosensor 100 is accommodated.

The portable terminal receiving portion 220 receives therein a portion of the portable terminal 300, that is, an upper portion of the portable terminal 300 where a camera 310 and a flash 320 are positioned.

The biosensor receiving portion 230 includes a sensor receiving cover 231 defining an inner space accommodating the biosensor 100 therein and protruding outwardly from the other surface of the partitioning wall 210, and a biosensor support 232 disposed in the inner space defined by the sensor receiving cover 231 and facing the light-receiving channel 250, wherein the biosensor 100 is mounted in the biosensor support 232.

The sensor receiving cover 231 has a sensor receiving opening 231a formed in a side portion thereof. The biosensor support 232 may be provided in a rail manner extending from the sensor receiving opening 231a to the inner space defined by the sensor receiving cover 231, such that the biosensor 100 may be slidably inserted into the biosensor support 232.

The light exit channel 240 may be disposed to face the flash 320 of the portable terminal 300 inserted into the portable terminal receiving portion 220, and may be embodied as a first opening formed in the partitioning wall 210 such that light from the flash passes therethrough. The first opening may have a shape corresponding to a shape of the flash 320. The light emitted from the flash may be introduced into the first opening, and the introduced light may be irradiated toward the biosensor support 232.

The light-receiving channel 250 is disposed so as to face the camera 310 of the portable terminal 300 inserted into the portable terminal receiving portion 220. The light-receiving channel 250 may be a second opening formed in the partitioning wall 210 such that the camera 310 is exposed to the partitioning wall 210.

Figure 4:
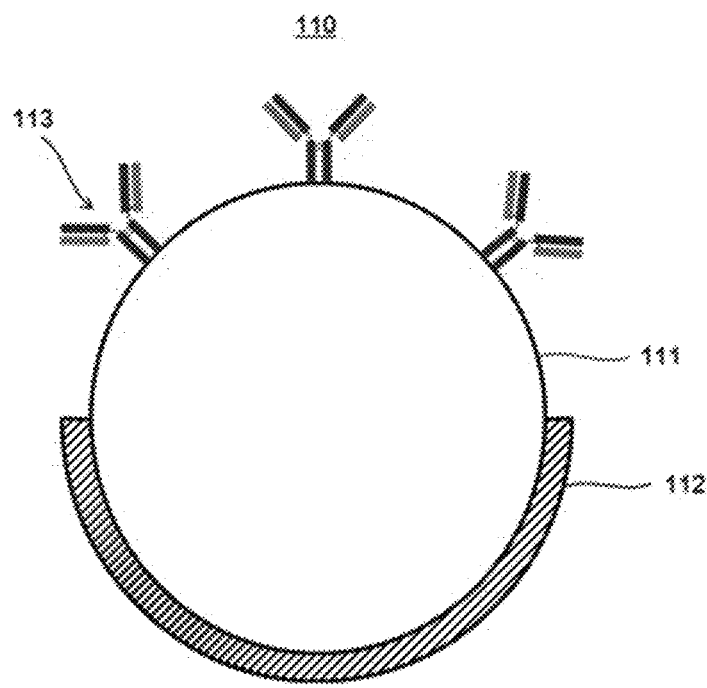
FIG. 4 and FIG. 5 are cross-sectional views to illustrate a biosensor shown in FIG. 1.
Figure 5:
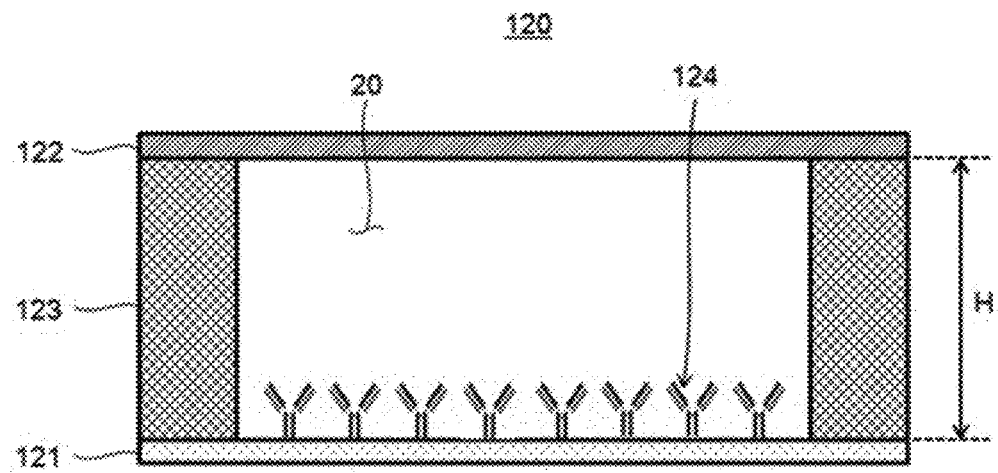

FIG. 4 and FIG. 5 are cross-sectional views to illustrate a biosensor shown in FIG. 1.

The biosensor 100 may include retroreflective Janus particles (RJPs) 110 and a sensing substrate 120.

The retroreflective Janus particle 110 may selectively react with a target bio-substance and retroreflect incident light thereto toward a light source.

In one embodiment, the retroreflective Janus particle 110 may include a transparent core particle 111, a total-reflective coating layer 112 covering a portion of the core particle 111, and a first biorecognition substance 113 directly or indirectly coupled to an exposed surface of the core particle 111.

The core particle 111 may have a spherical shape. In the present disclosure, the terms 'spherical' is defined to include not only a perfect sphere in which radii from a center to all points on a surface thereof are equal to each other, but also a substantial sphere in which a difference between maximum and minimum radii among radii from a center to all points on a surface thereof is smaller than or equal to about 10%. The core particle 111 may have an average diameter of about 600 nm to 5 μm, for example, about 700 nm to 900 nm in consideration of binding characteristics to the target bio-substance (not shown), a relationship with a wavelength of the light emitted from the light source, and sedimentation characteristics in a detection target solution.

In one embodiment, the core particle 111 may be made of a transparent material capable of transmitting incident light therethrough. For example, the core particle 111 may be made of a transparent oxide or a transparent polymer. The transparent oxide may include, for example, silica, glass, and the like, and the transparent polymer may include, for example, polystyrene, polymethyl methacrylate, and the like.

The total-reflective coating layer 112 may be formed to cover a portion of a surface of the core particle 111, and may totally reflect at least a portion of the light traveling inside the core particle 111 to increase an amount of light retroreflected toward the light source, that is, the flash 320 and the camera 310.

In one embodiment, the total-reflective coating layer 112 may be formed on the surface of the core particle 111 so as to cover about 30% to 70% of the surface of the core particle 111. When the total-reflective coating layer 112 covers a portion smaller than 30% of the surface of the core particle 111, an amount of a portion of the light incident into the core particle 111 that is not retroreflected but leaks is large, the sensitivity of the biosensor 100 may be lowered. When the total-reflective coating layer 112 covers a portion larger than 70% of the surface of the core particle 111, an amount of light incident into the inside of the core particle 111 is reduced, resulting in decrease in the sensitivity of the biosensor 100. In one embodiment, the total-reflective coating layer 112 may be formed on the surface of the core particle 111 so as to cover about 40% to 60% of the surface of the core particle 111.

In one embodiment, the total-reflective coating layer 112 may be made of a material having a lower refractive index than that of the core particle 111 in order to totally reflect at least a portion of the light traveling inside the core particle 111 to increase the amount of the portion which is retroreflected toward the light source. In one example, the core particle 111 may be made of a material having a refractive index of about 1.4 or greater in a visible light wavelength region of at least 360 nm to 820 nm. The total-reflective coating layer 112 may be made of a material having a refractive index lower than that of the core particle 121. Specifically, when the core particle 111 is made of a transparent oxide or transparent polymer having a refractive index of about 1.4 or greater in the visible ray region, the total-reflective coating layer 112 may be made of a metal material having the refractive index lower than the refractive index of about 1.4 or greater in the visible ray region. For example, the total-reflective coating layer 112 may be made of at least one metal selected from gold (Au) having a refractive index of about 0.22, silver (Ag) having a refractive index of about 0.15, aluminum (Al) having a refractive index of about 1.0, copper (Cu) having a refractive index of about 0.4, and zinc (Zn) having a refractive index of about 1.2, etc. relative to light of a wavelength of 532 nm.

In one embodiment, in order to prevent light leakage due to light transmission and improve dispersibility of the retroreflective Janus particles 110 in the detection target solution, the total-reflective coating layer 112 may have a thickness of about 10 to 500 nm. When the thickness of the total-reflective coating layer 112 is smaller than 10 nm, a portion of the light incident into the core particle 111 may travel through the total-reflective coating layer 112 and thus may leak. When the thickness of the total-reflective coating layer 112 exceeds 500 nm, the retroreflective Janus particle 110 may increase in weight and the dispersibility of the retroreflective Janus particles 110 in the liquid may decrease.

The first biorecognition substance 113 may be made of a material capable of selectively binding to a target bio-substance. The first biorecognition substance 113 may be changed according to a target bio-substance to be detected, and may include one or more selected from proteins, nucleic acids, and ligands. For example, when the target bio-substance is an antigen substance, the first biorecognition substance 113 may be an antibody or aptamer substance that specifically reacts with the antigen substance. When the target bio-substance is a genetic substance, the first biorecognition substance 113 may be a nucleic acid substance such as DNA (deoxyribonucleic acid), RNA (ribonucleic acid), or PNA (peptide nucleic acid) capable of complementary binding to the genetic substance. When the target bio-substance is a cell signal substance, the first biorecognition substance 113 may be a chemical ligand substance that selectively binds to the cell signal substance.

The first biorecognition substance 113 may be directly or indirectly bonded to an exposed surface of the core particle 111 not covered with the total-reflective coating layer 112. In one embodiment, the first biorecognition substance 113 may be selectively modified only onto the exposed surface of the core particle 111 and may not be modified onto the surface of the total-reflective coating layer 112. For example, in a process of manufacturing the retroreflective Janus particle, a material preventing the biorecognition substance from being modified on the surface, such as 6-mercapto-1-hexanol, 2-mercaptoethanol, 3-mercapto-1-propanol, 4-mercapto-1 butanol, 6-mercapto-1-hexanol, or thiol-PEG are first applied to the surface of the total-reflective coating layer 112. Then, the retroreflective Janus particles are added to a high-concentration solution containing the biorecognition substance, such that only the exposed surface of the core particle 111 may be modified with the biorecognition substance. In this way, the first biorecognition substance 113 is selectively modified only onto the exposed surface of the core particle 111, such that the exposed surface of the core particle 111 may be directed so as to face the camera 310 of the portable terminal 300. Thus, a stronger retroreflected signal may be induced, and as a result, the sensitivity of the biosensor 100 may be improved.

The sensing substrate 120 may include a sealed fluid channel 20 accommodating the detection target solution containing the target bio-substance and the retroreflective Janus particle 110 binding to the target bio-substance. One surface of the fluid channel 20 may be modified with a second biorecognition substance 124 that selectively binds to the target bio-substance.

In one embodiment, the sensing substrate 120 may include a bottom 121, a cover 122, a sidewall 123, and the second biorecognition substance 124.

The bottom 121 may be made of a transparent polymer material and may constitute a bottom surface of the fluid channel 20. In one embodiment, the bottom 121 may be made of a transparent polymer material such as PMMA (poly methyl methacrylate), PC (polycarbonate), or PS (polystyrene).

The cover 122 is disposed so as to face the bottom while being spaced apart therefrom and may constitute an upper surface of the fluid channel 20, and may have an injection hole (not shown) through which the detection target solution may be injected into the fluid channel 20. The cover 122 may be made of the same material as that of the bottom 121 or may be made of a different material therefrom. In one embodiment, the cover 122 may be made of PDMS (polydimethylsiloxane), PS (polystyrene), PMMA (poly methyl methacrylate), COC (cyclic olefin copolymer), COP (cyclic olefin polymer), or the like.

The sidewall 123 may have a through opening defined therein corresponding to the fluid channel 20 and may be disposed between the bottom 121 and the cover 122 and may constitute a side surface of the fluid channel 20. The sidewall 123 may be integrally formed with the bottom 121 and may be made of the same material as that of the bottom 121, or may be made of a material different from that of the bottom 121.

Since a height H of the fluid channel 20 is related to a dimension by which the retroreflective Janus particle settles in the detection target solution, the height of the fluid channel 20 may be in a range of about 50 to 1000 μm.

The second biorecognition substance 124 may be modified onto a surface of the bottom 121 corresponding to the bottom surface of the fluid channel. The second biorecognition substance 124 may be made of a material capable of selectively binding to the target bio-substance. The second biorecognition substance 124 may be made of the same material as that of the first biorecognition substance 113 of the retroreflective Janus particle 110 or may be made of a different material therefrom. The second biorecognition substance 124 may be changed according to the target bio-substance to be detected, and may include one or more selected from proteins, nucleic acids, and ligands. For example, when the target bio-substance is an antigen substance, the second biorecognition substance 124 may be an antibody or aptamer substance that specifically reacts with the antigen substance. When the target bio-substance is a gene substance, the second biorecognition substance 124 may be a nucleic acid substance such as DNA (deoxyribonucleic acid), RNA (ribonucleic acid), PNA (peptide nucleic acid), etc. capable of complementary binding to the gene substance. When the target bio-substance is a cell signal substance, the second biorecognition substance 124 may be a chemical ligand substance that selectively binds to the cell signal substance.

When the biosensor 100 is accommodated in the biosensor receiving portion 230, the bottom 121 is accommodated in the biosensor receiving portion 230 so as to face the light exit channel 240 and the light-receiving channel 250.

Figure 6:
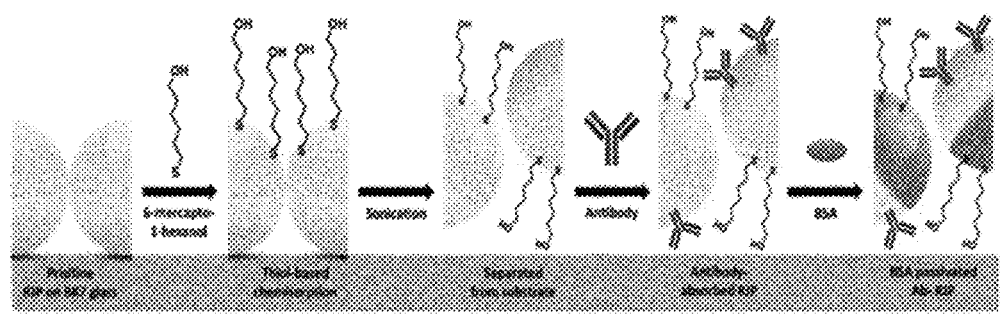
FIG. 6 is a diagram for illustrating an embodiment of a method of selectively modifying an exposed surface of a core particle of a retroreflective Janus particle with a first biorecognition substance.

FIG. 6 is a diagram for illustrating an embodiment of a method of selectively modifying an exposed surface of a core particle of a retroreflective Janus particle with a first biorecognition substance.

Referring to FIG. 6, single-layer core particles may be arranged, at high density, on a substrate, and then a total-reflective coating layer may be formed on a hemispherical surface of each of the core particles using an ion beam deposition scheme.

Then, passivation may be performed by modifying an alkanethiol compound capable of serving as a spacer onto a surface of the total-reflective coating layer, and then the particles may be removed from the substrate. For example, the alkanethiol compound may include a compound such as 6-mercapto-1-hexanol, 2-mercaptoethanol, 3-mercapto-1-propanol, 4-mercapto-1-butanol, 6-mercapto-1-hexanol, thiol-PEG, etc.

Subsequently, the particles in which the total-reflective coating layer is passivated with the alkanethiol compound may be added into a solution containing a high concentration of the first biorecognition substance. Thus, the first biorecognition substance may be adsorbed on the exposed surface of the core particle.

Subsequently, in order to minimize non-specific binding of the target bio-substance to the retroreflective Janus particle, BSA (Bovine Serum Albumin) may be selectively coated on a portion of the surface of the particle onto which the total reflective coating layer is not modified.

Figure 7:
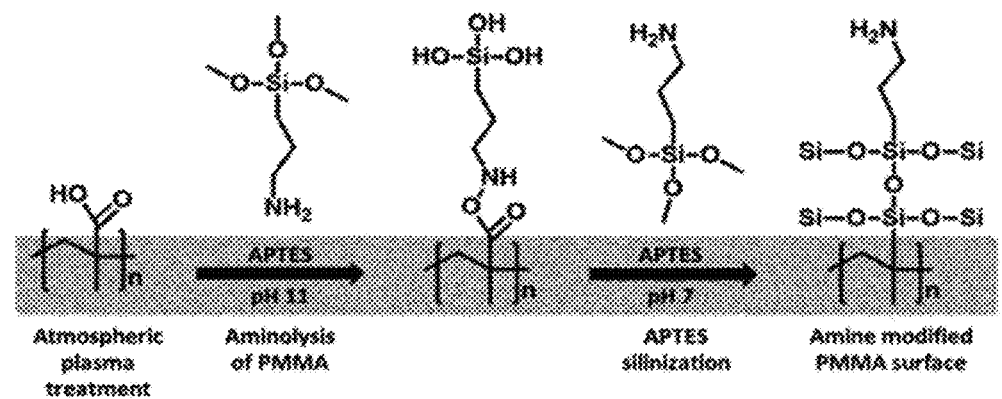
FIG. 7 is a diagram for illustrating an embodiment of a surface treatment process for fixing a second biorecognition substance onto a bottom of a sensing substrate made of PMMA.

FIG. 7 is a diagram for illustrating an embodiment of a surface treatment process for fixing a second biorecognition substance onto a bottom of a sensing substrate made of PMMA.

Referring to FIG. 7, a carboxyl group may be modified onto the PMMA substrate by performing atmospheric pressure plasma treatment on the PMMA substrate.

Subsequently, silanization may be repeatedly performed via an aminolysis reaction. At this time, an amine group may be modified onto the surface so as to be exposed to an outside.

Subsequently, the second biorecognition substance may be fixed to the surface of the PMMA substrate using a cross-linker compound reacting with the amine group and the second biorecognition substance. For example, when the second biorecognition substance is an antibody substance, Glutaraldehyde and succinimidyl ester-based compounds may be used as the cross-linker compound. For example, a BS3 (bis(sulfosuccinimidyl)suberate) compound may be used as the cross-linker compound.

In one embodiment, a downloadable application may be installed in the portable terminal 300 and may analyze a bio-substance from the biosensor 100.

In one embodiment, the application may include an image generator for imaging the retroreflected optical signal, an image processor for processing the image generated by the image generator, and an image analyzer for analyzing the image processed by the image processor.

The image generator may generate a plurality of continuously photographed images for a predetermined time using a time-lapse technique. For example, the image generator may continuously capture about 4 or more pictures related to the retroreflected optical signal for about 1 to 2 seconds and may create the images thereof.

The image processor may analyze the plurality of continuously photographed images, and then may maintain static pixels whose values do not change for a predetermined time period, and may remove dynamic pixels whose values have undergone changes. When the image is processed in this way, errors caused by light retroreflected from unreacted retroreflective Janus particles may be minimized.

The image analyzer may analyze the image processed by the image processor and generate quantitative information such as a concentration of the target bio-substance based on the analysis result. For example, the image analyzer may generate the quantitative information of the target bio-substance based on a calculating result of the number of retroreflective Janus particles from the image.

Moreover, the application may drive the camera 310 and the flash 320 of the portable terminal 300.

Figure 8:
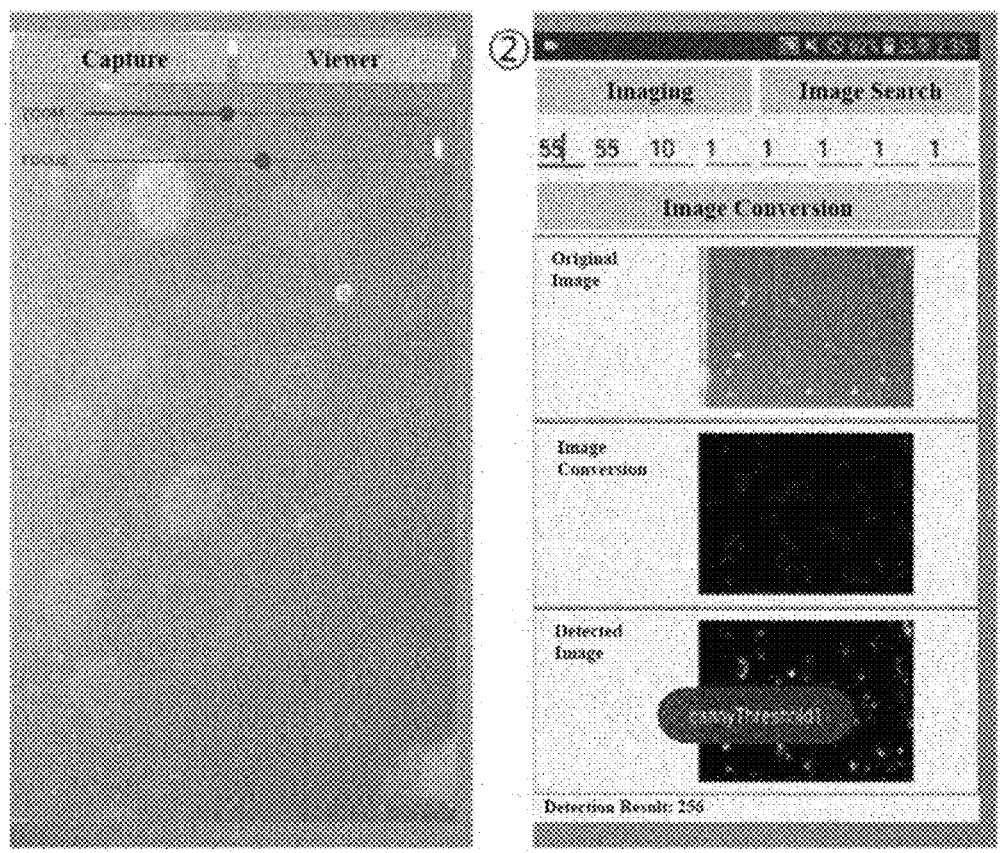
FIG. 8 shows a state in which an application is executed in a portable terminal combined with a gadget for retroreflected signal measurement according to an embodiment of the present disclosure.

FIG. 8 shows a state in which an application is executed in a portable terminal combined with a gadget for retroreflected signal measurement according to an embodiment of the present disclosure.

Referring to FIG. 8, the application may provide an interface on which an operator may adjust a magnification and a focus of the camera 310 of the portable terminal 300, and may display a result value about quantitative information of the target bio-substance obtained from the image.

In one embodiment, the gadget for measuring a retroreflected signal according to an embodiment of the present disclosure may further include a magnifying lens 260 and a light outlet channel 270.

The magnifying lens 260 may be disposed between the second opening as the light-receiving channel 250 and the biosensor 100. The magnifying lens 260 may be embodied as a manual zoom lens. The magnifying lens 260 may be provided to cope with a case where the zoom function of the camera of the portable terminal 300 is deteriorated or a magnifying function thereof is not activated. Accordingly, when the magnifying function of the camera in the portable terminal 300 is not effective or does not work, the bottom 121 of the sensing substrate 120 of the biosensor 100 may be captured in a magnified manner using the magnifying lens 260.

The light outlet channel 270 is disposed behind the biosensor receiving portion 230 and faces the biosensor receiving portion 230. In one embodiment, the light outlet channel 270 may be a third opening formed in a rear portion of the sensor receiving cover 231. The third opening may have a length greater than or equal to a length of the biosensor support 232. The light outlet channel 270 may prevent a problem that when light is irradiated from the flash of the portable terminal 300, the light is reflected from an inner surface of the sensor receiving cover 231, and thus, when the camera of the portable terminal 300 captures the sensing substrate 120 of the biosensor 100, a background of the image is excessively bright due to an excessive amount of light, such that the number of retroreflective Janus particles is not accurately calculated from the image.

Hereinafter, a process of analyzing a bio-substance using a gadget for measuring a retroreflected signal according to an embodiment of the present disclosure will be described.

Figure 9:
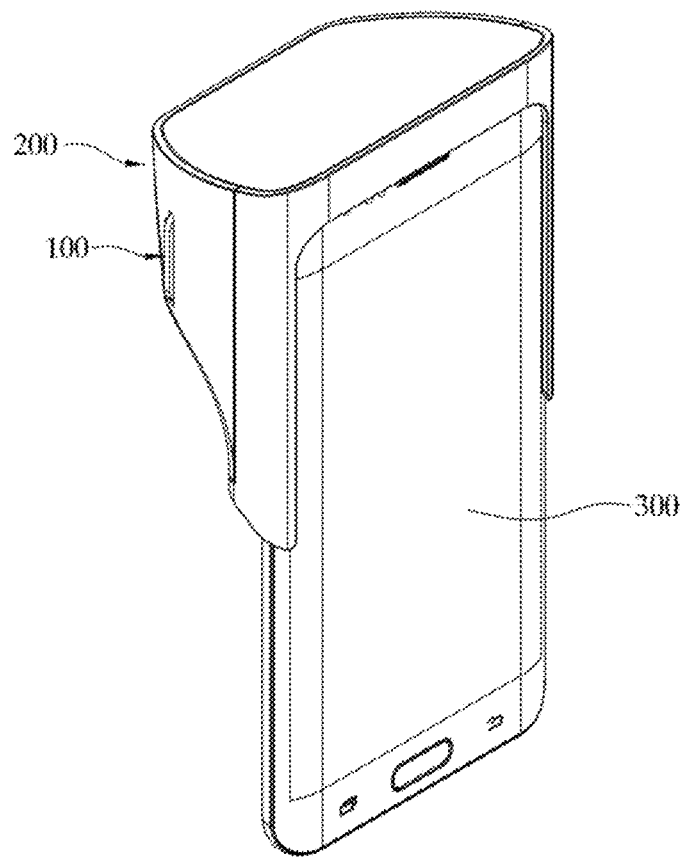
FIG. 9 is a perspective view showing a state in which a gadget for measuring a retroreflected signal according to an embodiment of the present disclosure is combined with a portable terminal.

FIG. 9 is a diagram showing a state in which a gadget for measuring a retroreflected signal according to an embodiment of the present disclosure is coupled to a portable terminal.

First, the gadget for retroreflected signal measurement is combined with the portable terminal 300 as shown in FIG. 9. In this regard, an upper portion of the portable terminal 300 where the camera and the flash of the portable terminal 300 are located is inserted into the portable terminal receiving portion 220. Thus, the gadget for measuring the retroreflected signal is coupled to the portable terminal 300. When the upper end of the portable terminal 300 is inserted into the portable terminal receiving portion 220 in this way, the light exit channel 240 faces the flash, while the light-receiving channel 250 faces the camera.

Figure 10:
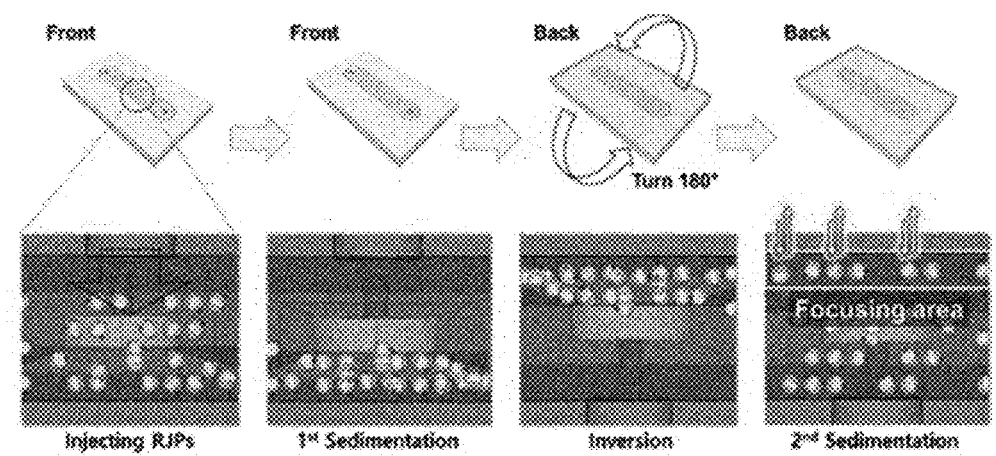
FIG. 10 is a diagram to illustrate settlement of retroreflective Janus particles under rotation of a sensing substrate.

FIG. 10 is a diagram to illustrate settlement of the retroreflective Janus particles under rotation of the sensing substrate.

Next, the retroreflective Janus particles 110 modified with the first biorecognition substance 113 that selectively reacts with the target bio-substance are added into the detection target solution containing the target bio-substance.

In this step, the retroreflective Janus particles 110 may be mixed with the detection target solution containing the target bio-substance, such that the first biorecognition substance 113 of the retroreflective Janus particle 110 may react with the target bio-substance. In this case, a sufficient number of retroreflective Janus particles may be mixed with the detection target solution so that an entire amount of the target bio-substances may react with the retroreflective Janus particles 110.

Next, the sensing substrate 120 is oriented so that the bottom 121 modified with the second biorecognition substance 124 that selectively reacts with the target bio-substance is positioned below the cover 122 in the direction of gravity. Subsequently, the detection target solution mixed with the retroreflective Janus particles 110 is injected into the fluid channel 20 of the sensing substrate 120. The solution is maintained therein for a first time duration.

In these steps, while the sensing substrate 120 is oriented so that the bottom 121 modified with the second biorecognition substance 124 is positioned below the cover 122 in the direction of gravity, the detection target solution containing the retroreflective Janus particles 110 and the target bio-substance which has reacted therewith is injected into the fluid channel through the detection target solution injection hole (not shown) formed in the cover. In this case, due to gravity, the retroreflective Janus particles 110 settle downward, that is, toward the bottom 121 of the sensing substrate 120. As a result, a selective reaction between the second biorecognition substance modified on the bottom 121 and the target bio-substance coupled to the retroreflective Janus particles 110 occurs. That is, the retroreflective Janus particles 110 that have reacted with the target bio-substance are fixed to the bottom 121 via the target bio-substance, while the retroreflective Janus particles 110 that do not react with the target bio-substance are not fixed to the bottom 121.

Next, the sensing substrate 120 is rotated so that the bottom 121 is located above the cover 122 in the direction of gravity, and then this state is maintained for a second time duration.

In this step, after the state in which the sensing substrate 120 is oriented so that the bottom 121 is located above the cover 122 in the direction of gravity has been maintained for the second time duration, the retroreflective Janus particles 110 fixed to the bottom 121 are maintained at relatively fixed positions, while the unreacted retroreflective Janus particles 110 not fixed to the bottom 121 sink downward due to gravity, that is, toward the cover 122.

The target bio-substance and the retroreflective Janus particles 110 react with each other. Then, after the second time duration has elapsed, the biosensor 100 may be accommodated in the biosensor receiving portion 230. Alternatively, before the second time duration has elapsed, the biosensor 100 may be received in the biosensor receiving portion 230, and then the second time duration may elapse.

The biosensor 100 is accommodated in the biosensor receiving portion 230 so that the bottom 121 of the sensing substrate 120 of the biosensor 100 faces the light exit channel 240 and the light-receiving channel 250. At the time, the biosensor 100 passes through the sensor receiving opening 231a of the sensor receiving cover 231 and is inserted into the biosensor support 232 and is received within the biosensor receiving portion 230.

Figure 11:
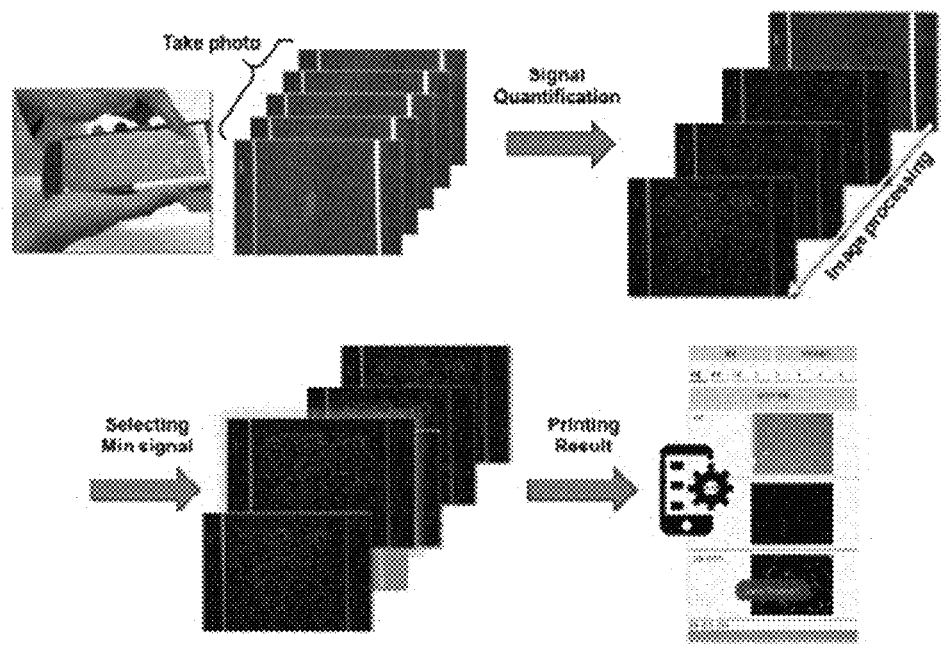
FIG. 11 is a diagram illustrating a process in which an application is executed to generate and analyze an image of light retroreflected from retroreflective Janus particles.

Next, in the state in which the biosensor 100 is accommodated in the biosensor receiving portion 230, the application downloaded to the portable terminal 300 is executed, such that light is irradiated into the fluid channel 20 through the bottom 121, and an image of the light retroreflected from the retroreflective Janus particles is generated and analyzed. FIG. 11 is a diagram illustrating a process in which the application is executed to generate and analyze the image of light retroreflected from the retroreflective Janus particles.

In this step, the executed application may display the image of the camera on an initial screen, and may display a bar-shaped controller using which the user may adjust the magnification and focus of the camera. After the user adjusts the magnification and focus of the camera of the portable terminal, the camera may capture the bottom 121 of the sensing substrate 120 of the biosensor 100. Then, the application may analyze a dot-shaped retroreflected signal.

In this regard, when the application turns on the flash of the portable terminal to irradiate the light into the fluid channel 20 through the bottom 121 of the sensing substrate 120 of the biosensor 100, the retroreflective Janus particles fixed to the bottom 121 may be fixed at a position adjacent to the bottom 121 to which the light is incident and may strongly retroreflect the incident light therefrom, whereas unreacted retroreflective Janus particles that are not fixed to the bottom 121 may settle down and weakly retroreflect the incident light in a suspended state.

Moreover, since the first biorecognition substance 113 is modified only onto the exposed surface of the core particle 111 of the retroreflective Janus particle 110, the retroreflective Janus particles 110 fixed to the bottom 121 are oriented so that the exposed surface of the core particle 111 thereof faces the bottom 121 of the sensing substrate 120. However, since the unreacted retroreflective Janus particles 110 that are not fixed to the bottom 121 are in the suspended state, the orientation directions thereof are irregular, and the orientation directions thereof may change over time.

In this way, in order to minimize analysis errors due to light retroreflected from the unreacted retroreflective Janus particles that are not fixed to the bottom 121, a plurality of consecutively photographed images, for example, 5 images may be generated for a predetermined time duration using a time-lapse technique, and then the static pixels whose values do not change for a predetermined time duration may be maintained, and the dynamic pixels whose values change, that is, in which blinking signals occur may be removed. In this way, the image may be processed. Then, the number of retroreflective Janus particles fixed to the bottom 121 may be calculated based on the processed image. Thus, the quantitative information such as the concentration of the target bio-substance, etc. may be generated based on the calculation result.

Finally, the application derives the image with the smallest number of blinking signals based on the retroreflected signal number data obtained through the above process.

According to the gadget for retroreflected signal measurement according to the present disclosure, the portable optical measurement equipment using retroreflection as a biosensing principle may be implemented so as not to employ fluorescence analysis used as a conventional optical analysis principle. Further, the gadget for retroreflected signal measurement may be simply connected to the portable terminal carried by an individual and may be capable of quantitative analysis of the target bio-substance via the biosensor using the retroreflective Janus particles (RJP) causing retroreflection as a signal probe, and thus may be used as an on-site diagnosis type analysis equipment.

Quantitative Analysis of CK-MB Marker

The target bio-substance was CK-MB as a biomarker for myocardial infarction. Thus, each of the retroreflective Janus particle and the sensing substrate was modified with anti-CKMB antibodies to form immune complexes. Samples were prepared by adding CK-MB protein at each of concentrations of 0, 0.1, 1, 10, 100, and 1000 ng/mL to human serum. In accordance with a process of analyzing the bio-substance as described above, the sample was reacted with the retroreflective Janus particles, and then was injected into the biosensor and was reacted therewith. Then, the biosensor was inserted into the biosensor receiving portion of the gadget. Then, the application was executed to quantify the retroreflected signal detected on the surface of the sensing substrate.

Figure 12:
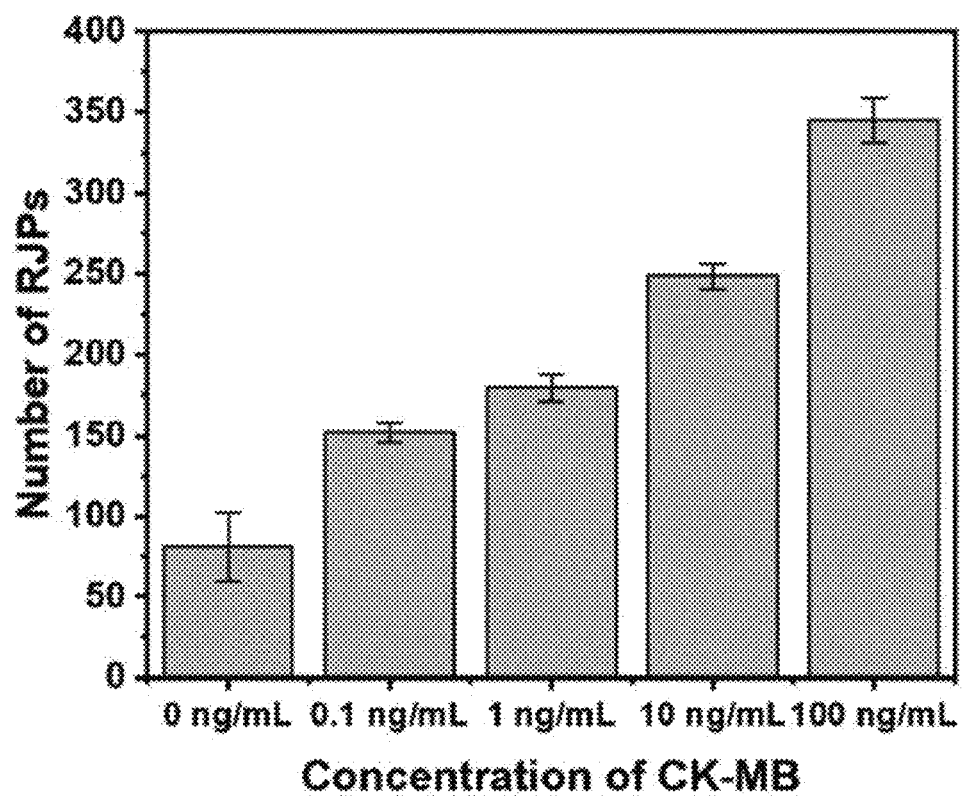
FIG. 12 is a graph showing a result of CK-MB immunoassay.

FIG. 12 is a graph showing the result of CK-MB immunoassay.

It was identified based on the calculation result by the application's image analyzer that as the concentration of the CK-MB protein added to human serum increased, the number of retroreflective Janus particles reacting with the target bio-substance on the biosensor surface increased. Moreover, the fact that a difference between retroreflective quantification results of the human serum sample having 0.1 ng/mL CK-MB added thereto and the human serum sample without CK-MB added thereto is statistically significant indicates that a minimum detection limit concentration is 0.1 ng/mL or smaller.

The descriptions of the presented embodiments are provided so that a person skilled in the art may use or practice the present disclosure. Various modifications to these embodiments will be apparent to those skilled in the art. The general principles defined herein may be applied to other embodiments without departing from the scope of the present disclosure. Thus, the present disclosure should not be limited to the embodiments presented herein, but should be interpreted in the widest scope consistent with the principles and novel features presented herein.

What is claimed is:

1. A gadget for measuring a retroreflected signal, the gadget comprising:
    a partitioning wall;
    a portable terminal receiving portion disposed on one surface of the partitioning wall;
    a biosensor receiving portion disposed on the other surface of the partitioning wall and constructed to receive a biosensor therein;
    a light exit channel defined in the partitioning wall and at one side thereof; and
    a light-receiving channel adjacent to the light exit channel and defined in the partitioning wall,
    wherein light passes through the light exit channel and then is reflected from the biosensor, and then is incident into the light-receiving channel, and
    wherein the gadget further comprises a light outlet channel disposed behind the biosensor receiving portion and disposed so as to face the biosensor receiving portion.

2. The gadget for measuring the retroreflected signal of claim 1, wherein the biosensor includes retroreflective Janus particles, and a sensing substrate,
    wherein each of the retroreflective Janus particles includes:
        a transparent core particle;
        a total-reflective coating layer covering a portion of the core particle; and
        a first biorecognition substance directly or indirectly binding to an exposed surface of the core particle,
    wherein the sensing substrate includes:
        a transparent bottom whose a surface is modified with a second biorecognition substance selectively reacting with a target bio-substance;
        a cover opposite to the bottom and having an injection hole defined therein through which a detection target solution is injected into the sensing substrate;
        a sidewall disposed between the cover and the bottom, and having a through opening defined therein; and
        a fluid channel defined by the bottom, the cover and the sidewall,
    wherein each of the retroreflective Janus particles is oriented so that the exposed surface of the core particle thereof faces the bottom of the sensing substrate,
    wherein the biosensor is accommodated in the biosensor receiving portion so that the bottom faces the light exit channel and the light-receiving channel.

3. The gadget for measuring the retroreflected signal of claim 1, wherein the portable terminal receiving portion accommodates therein an upper end of the portable terminal where a camera and a flash of the portable terminal are disposed,
    wherein the light exit channel is disposed so as to face the flash,
    wherein the light-receiving channel is disposed so as to face the camera.

4. The gadget for measuring the retroreflected signal of claim 3, wherein the light exit channel acts as a first opening through which light from the flash passes through the partitioning wall,
    wherein the light-receiving channel acts as a second opening through which light passes through the partitioning wall and is incident to the camera.

5. The gadget for measuring the retroreflected signal of claim 4, wherein the gadget further comprises a magnifying lens disposed between the second opening and the biosensor.

6. The gadget for measuring the retroreflected signal of claim 1, wherein the biosensor receiving portion includes:
    a sensor receiving cover protruding outwardly from the other surface of the partitioning wall, wherein an inner space is defined by the cover and accommodates the biosensor therein; and
    a biosensor support disposed in the inner space defined by the sensor receiving cover and disposed so as to face the light-receiving channel, wherein the biosensor is mounted into the biosensor support.

7. The gadget for measuring the retroreflected signal of claim 6, wherein the sensor receiving cover has a sensor receiving opening defined in a side portion thereof,
  wherein the biosensor support has a rail structure extending from the sensor receiving opening to the inner space defined by the sensor receiving cover, wherein the biosensor is slidably inserted into the rail structure.

8. The gadget for measuring the retroreflected signal of claim 6, wherein the light outlet channel is defined in a rear portion of the sensor receiving cover.

9. The gadget for measuring the retroreflected signal of claim 8, wherein the light outlet channel acts as a third opening disposed in the rear portion of the sensor receiving cover.

10. The gadget for measuring the retroreflected signal of claim 9, wherein the third opening has a length greater than or equal to a length of the biosensor support.

\* \* \* \* \*